United States Patent
Tsai et al.

(10) Patent No.: US 8,377,660 B2
(45) Date of Patent: Feb. 19, 2013

(54) METHOD FOR PRODUCING AN OPTICALLY ACTIVE COMPOUND

(75) Inventors: Shau-Wei Tsai, Tainan (TW); Pei-Yun Wang, Sanchong (TW)

(73) Assignee: Chang Gung University, Kwei-Shan, Tao-Yuan (TW)

( * ) Notice: Subject to any disclaimer, the term of this patent is extended or adjusted under 35 U.S.C. 154(b) by 176 days.

(21) Appl. No.: 12/731,558

(22) Filed: Mar. 25, 2010

(65) Prior Publication Data

US 2011/0045551 A1  Feb. 24, 2011

(30) Foreign Application Priority Data

Aug. 21, 2009  (TW) .............................. 98128247 A

(51) Int. Cl.
*C12P 17/10* (2006.01)
(52) U.S. Cl. ....................................................... 435/121
(58) Field of Classification Search .................. None
See application file for complete search history.

(56) References Cited

PUBLICATIONS

Wang et al., "(R,S)-Azolides as Novel Substrates for Lipase-Catalyzed Hydrolytic Resolution in Organic Solvents," Adv. Synth. Catal., vol. 351, pp. 2333-2341 (published online Sep. 23, 2009).*
Wu et al., "Improvements of enzyme activity and enantioselectivity in lipase-catalyzed alcoholysis of (R,S)-azolides," Journal of Molecular Catalysis B: Enzymatic, vol. 62, pp. 235-241 (published online Nov. 10, 2009).*
Sigma Aldrich MSDS for Novozyme 435 (immobilized on acrylic resin) 5 pages total (updated Jan. 26, 2006).*

* cited by examiner

*Primary Examiner* — Sharmila G. Landau
*Assistant Examiner* — Paul D. Pyla
(74) *Attorney, Agent, or Firm* — Occhiuti Rohlicek & Tsao LLP

(57) ABSTRACT

A method for producing an optically active compound includes reacting a nucleophile with a mixture of R- and S-stereoisomers of an azolide substrate by enzyme-catalyzed kinetic resolution so as to produce the optically active compound, wherein the azolide substrate contains an azole group used as a leaving group and an acyl group directly bonded to a nitrogen atom of the azole group.

18 Claims, No Drawings

METHOD FOR PRODUCING AN OPTICALLY ACTIVE COMPOUND

CROSS-REFERENCE TO RELATED APPLICATION

This application claims priority of Taiwanese Application No. 098128247, filed on Aug. 21, 2009.

BACKGROUND OF THE INVENTION

1. Field of the Invention

This invention relates to a novel method for producing an optically active compound, more particularly to a method for producing an optically active compound by enzyme-catalyzed kinetic resolution.

2. Description of the Related Art

Optically active compounds are usually prepared by enzyme-catalyzed kinetic resolution of R- and S-stereoisomers of a substrate through hydrolysis, esterification, trans-esterification, or aminolysis. The enatioselectivity of the stereoisomers in the kinetic resolution depends mainly on the rate-limiting formation and breakdown of a tetrahedral intermediate in the reaction.

Many studies have focused on the types of enzyme catalysts and the types of solvents to be used in a reaction system of the enzyme-catalyzed kinetic resolution so as to improve the productivity and enatioselectivity of the optically active compound to be obtained.

U.S. Pat. No. 6,201,151 discloses a process for preparing optically active (S)-α-arylpropionic acids or esters by kinetic resolution of racemic arylpropionic acid in an organic solvent in the presence of an enzyme catalyst. Taiwanese Patent No. 1276687 discloses a kinetic resolution of α-substituted acetic acids or esters in an organic solvent in the presence of *Carica papaya* lipase.

Although the productivity and enatioselectivity of the optically active compound can be improved by selecting suitable enzyme catalyst and solvent, the improvement is still poor.

SUMMARY OF THE INVENTION

Therefore, an object of the present invention is to provide a novel method for producing an optically active compound. The method can achieve a high enatioselectivity (i.e., enantiomeric ratio), a better conversion, a high optical purity of substrate or product (i.e., enantiomeric excess, ee value), and a short reaction time in the production of the optically active compound.

According to this invention, there is provided a method for producing an optically active compound. The method comprises reacting a nucleophile with a mixture of R- and S-stereoisomers of an azolide substrate by enzyme-catalyzed kinetic resolution so as to produce the optically active compound, wherein the azolide substrate contains an azole group used as a leaving group and an acyl group directly bonded to a nitrogen atom of the azole group.

DETAILED DESCRIPTION OF THE PREFERRED EMBODIMENTS

This invention relates to a method including the step of reacting a nucleophile with a mixture of R- and S-stereoisomers of an azolide substrate by enzyme-catalyzed kinetic resolution so as to produce the optically active compound, wherein the azolide substrate contains an azole group used as a leaving group and an acyl group directly bonded to a nitrogen atom of the azole group.

Preferably, the azolide substrate is represented by Formula (I):

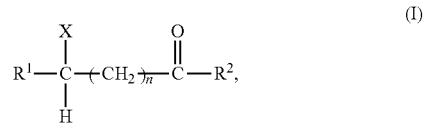

wherein

X represents a halogen atom, methyl, ethyl, methoxy, ethoxy, —OH, —NH$_2$, —NHCOCH$_3$, —SH, or —SCH$_3$;

R$^1$ is different from X and represents a straight-chain or branched saturated or unsaturated C$_1$-C$_{20}$ aliphatic group, an aryl group, an aryloxy group or a C$_3$-C$_{12}$ heterocyclic group containing one to three heteroatoms selected from O, S and N, each group being optionally substituted with one to three substituents selected from the group consisting of a halogen atom, an aryl group, an aryloxy group, —NH$_2$, —CF$_3$, —CN, —NO$_2$, —OH, —SH, —COOH, —SCF$_3$, —OCF$_3$, —CONH$_2$, —COC$_6$H$_5$, a C$_1$-C$_6$ alkyl group and a C$_1$-C$_6$ alkoxy group;

R$^2$ represents an azole group optionally substituted with one or two substituents selected from the group consisting of a halogen atom, an aryl group, an aryloxy group, —NH$_2$, —CF$_3$, —CN, —NO$_2$, —OH, —SH, —COOH, —SCF$_3$, —OCF$_3$, —CONH$_2$, a C$_1$-C$_6$ alkyl group and a C$_1$-C$_6$alkoxy group; and n is 0 or 1.

Unlike normal amides, which have a poor reactivity in the nucleophilic reaction, the azolide substrate, which is a heterocyclic amide, has a high reactivity attributed to an unshared electron pair on the nitrogen that is directly bonded to the acyl group and that is part of the cyclic π-system of the azole group of the azolide substrate. The special structure leads to a partial positive charge on the nitrogen (N1) that is directly bonded to the acyl group. The nitrogen with partial positive charge makes the azole group to be a better leaving group and exerts an electron-withdrawing effect on the carbonyl group of the acyl group of the azolide substrate, thereby enhancing the formation and breakdown of the tetrahedral intermediate, i.e., improve the nucleophilic reaction of the carbonyl group of the azolide substrate, during the enzyme-catalyzed kinetic resolution of the substrate.

The term "aliphatic group" as used herein includes, but is not limited to, straight-chain or branched saturated or unsaturated alkyl groups, alkenyl groups, alkynyl groups and cycloalkyl groups. The term "aryl group" as used herein includes, but is not limited to, phenyl, naphthyl, biphenyl, etc. The term "heterocyclic group" as used herein includes, but is not limited to, thienyl, furyl, pyridyl, pyrazinyl, imidazolyl, pyranyl, etc.

Preferably, the substrate is a racemic mixture of R- and S-stereoisomers of the azolide substrate (i.e., the substrate contains R- and S-stereoisomers in the same amount).

The racemic mixture of the azolide substrate may be prepared through a conventionally known process, such as the following two methods: method (I)—reacting a racemic mixture of a carboxylic acid with an azole in the presence of triethylamine and thionyl chloride at room temperature for two hours, followed by purification so as to obtain the racemic mixture of the azolide substrate; and method (II)—reacting a racemic mixture of a carboxylic acid with N,N-carbonyl diazole under 55° C. for two hours, followed by cooling down the reaction temperature to 4° C., removing the unreacted N,N-carbonyl diazole and the side products, and drying the final product so as to obtain the racemic mixture of the azolide substrate.

Preferably, X of Formula (I) is a halogen atom, methyl, ethyl, methoxy, or ethoxy. In the preferred embodiments of this invention, X is bromine, methyl, ethyl, or methoxy.

Preferably, $R^1$ of Formula (I) is an optionally substituted aryl group, or a substituted aryloxy group. More preferably, $R^1$ is an optionally substituted phenyl group, an optionally substituted phenoxy group, or an optionally substituted naphthyl group. In the preferred embodiments of this invention, $R^1$ is phenyl, 2,4-dichlorophenoxy, 4-chlorophenoxy, 3-phenoxyphenyl, 4-fluorobiphenyl, 4-isobutylphenyl, 3-benzoylphenyl, or 6-methoxynaphthyl.

Preferably, $R^2$ of Formula (I) is an optionally substituted imidazolyl group, an optionally substituted pyrazolyl group, an optionally substitutedtriazolyl group, or an optionally substituted tetrazolyl group. In the preferred embodiments of this invention, $R^2$ is 1,2,4-triazolyl, 4-bromopyrazolyl, 4-methylpyrazolyl, 4-nitropyrazolyl, imidazolyl, pyrazolyl, 3-(2-pyridyl)pyrazolyl, 3-aminopyrazolyl, 3-methylpyrazolyl, 3-(3-bromophenyl)pyrazolyl, or 3-methyl-4-bromopyrazolyl.

In the preferred embodiments of this invention, the azolide substrate is N-2-phenylpropionyl-1,2,4-triazole, N-2-phenylpropionyl-4-bromopyrazole, N-2-phenylpropionyl-4-methylpyrazole, N-2-phenylpropionyl-4-nitropyrazole, N-2-phenylpropionyl-imidazole, N-2-phenylpropionyl-pyrazole, N-2-phenylpropionyl-3-(2-pyridinyl)pyrazole, N-2-(2,4-dichlorophenoxy)propionyl-4-bromopyrazole, N-2-(4-chlorophenoxy)propionyl-4-bromopyrazole, N-2-(3-phenoxyphenyl)propionyl-1,2,4-triazole, N-2-(4-fluorobiphenyl)propionyl-1,2,4-triazole, N-2-(4-isobutylphenyl)propionyl-1,2,4-triazole, N-2-(3-benzoylphenyl)propionyl-1,2,4-triazole, N-2-(6-methoxynaphthyl)propionyl-1,2,4-triazole, N-α-bromophenylacetyl-4-bromopyrazole, N-α-methoxyphenylacetyl-4-bromopyrazole, Nα-methoxyphenylacetyl-3-(2-pyridinyl)pyrazole, N-β-phenylbutyryl-4-bromopyrazole, N-α-bromophenylacetyl-1,2,4-triazole, N-2-phenylpropionyl-3-aminopyrazole, N-2-phenylpropionyl-3-methylpyrazole, N-2-phenylpropionyl-3-(3-bromophenyl)pyrazole, N-α-phenylpropionyl-3-methyl-4-bromopyrazole, N-α-ethylphenylacetyl-3-(2-pyridinyl)pyrazole, N-α-ethylphenylacetyl-1,2,4-triazole, N-α-methoxyphenylacetyl-1,2,4-triazole, N-α-bromophenylacetyl-3-methylpyrazole, N-2-(4-fluorobiphenyl)propionyl-4-bromopyrazole, N-2-(3-benzoylphenyl)propionyl-4-bromopyrazole, or N-2-(6-methoxynaphthyl)propionyl-4-bromopyrazole.

Preferably, the enzyme-catalyzed kinetic resolution of the racemic mixture of the azolide substrate is conducted in an organic solvent in the presence of a lipase that serves as an enzyme catalyst.

Preferably, the lipase is selected from the group consisting of *Candida rugosa* lipase, *Pseudomonas cepacia* lipase, *Candida antarctica* lipase B, and *Carica papaya* lipase. The above *Carica papaya* lipase may be prepared from latex exudates of a plant of *Carica papaya*, e.g., the exuded latex of the leaves, stems, immature fruits or the wounded surfaces of a plant of *Carica papaya*, or available from the commercial papain.

Optionally, the lipase may be carried on a support selected from the group consisting of an organic support (e.g., organic polymer, such as poly(acrylic acid)) and an inorganic support (e.g., ceramic, diatomite).

Preferably, examples of the organic solvent include, but are not limited to, isooctane, heptane, hexane, cyclohexane, cyclohexanone, pentane, toluene, benzene, isopropyl ether, methyl isobutyl ether, methyl t-butyl ether, dichloromethane, t-pentanol, and combinations thereof.

Preferably, the nucleophile is selected from the group consisting of water, an alcohol, an amine, and an ester based on the type of the reaction in the enzyme-catalyzed kinetic resolution.

In some preferred embodiments of this invention, the nucleophile is water, and the enzyme-catalyzed kinetic resolution is performed through stereoselective hydrolysis of the substrate in the organic solvent in the presence of the lipase. It is noted that the nucleophile can be contained in or mixed with the organic solvent, i.e., an organic solvent saturated with water, or a biphasic solution consisting of water and an organic solvent for the hydrolysis. The mechanism of the hydrolysis is as follows:

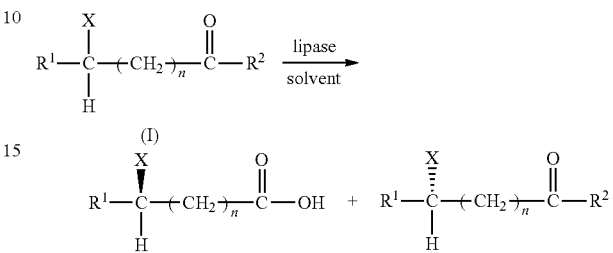

In other preferred embodiments of this invention, the nucleophile is an alcohol, and the enzyme-catalyzed kinetic resolution of the substrate is performed through stereoselective alcoholysis of the substrate in the organic solvent in the presence of the lipase. It is noted that the organic solvent is preferably an anhydrous organic solvent or an organic solvent containing trace water for the alcoholysis. The mechanism of the alcoholysis is as follows:

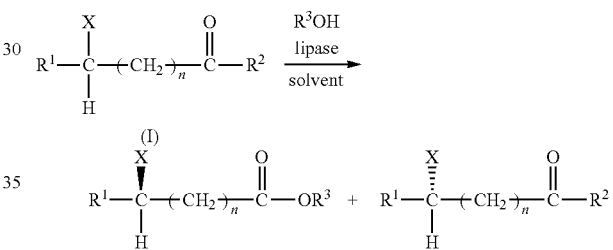

In alcoholysis, the alcohol is chosen according to what the final product is to be obtained. Preferably, the alcohol is methanol, ethanol, propanol, butanol, pentanol, hexanol, trimethylsilyl methanol, trimethylsilyl ethanol, or dimethylamino ethanol. In the preferred embodiments of this invention, the alcohol is methanol, ethanol, n-propanol, n-butanol, n-pentanol, n-hexanol, trimethylsilyl methanol, trimethylsilyl ethanol, or dimethylamino ethanol.

The temperature of the enzyme-catalyzed kinetic resolution depends on the type of the lipase used in the reaction system. Preferably, the enzyme-catalyzed kinetic resolution is conducted at a temperature ranging from 5° C. to 90° C.; and more preferably, from 15° C. to 55° C.

The following examples and comparative example are provided to illustrate the merits of the preferred embodiments of the invention, and should not be construed as limiting the scope of the invention.

EXAMPLE

Chemicals used in the Following Examples

1. Substrate:

A substrate specified in Table 1 was prepared by subjecting two reactants (I) and (II) specified in Table 1 for each substrate to reaction at room temperature or 55° C. When the reactant (II) was N,N-carbonyldi(1,2,4-triazole) or N,N-carbonyldiimidazole, the reaction was conducted at 55° C.

TABLE 1

| No. | Racemic Substrate | Reactant (I) | Reactant (II) |
|---|---|---|---|
| (1) | N-2-phenylpropionyl-1,2,4-triazole | 2-phenylpropionic acid (available from Fluck Co.) | N,N-carbonyldi(1,2,4-triazole) (available from Aldrich Co.) |
| (2) | N-2-phenylpropionyl-4-bromopyrazole | 2-phenylpropionic acid | 4-bromopyrazole(available from Aldrich Co.) |
| (3) | N-2-phenylpropionyl-4-methylpyrazole | 2-phenylpropionic acid | 4-methyl-pyrazole (available from Acros Co.) |
| (4) | N-2-phenylpropionyl-4-nitropyrazole | 2-phenylpropionic acid | 4-nitropyrazole(available from Matrix Scientific Co.) |
| (5) | N-2-phenylpropionyl-imidazole | 2-phenylpropionic acid | N,N-carbonyldi(imidazole) |
| (6) | N-2-phenylpropionyl-pyrazole | 2-phenylpropionic acid | pyrazole (available from Acros Co.) |
| (7) | N-2-phenylpropionyl-3-(2-pyridinyl)-pyrazole | 2-phenylpropionic acid | 3-(2-pyridinyl)-pyrazole (available from Alfa Aesar Co.) |
| (8) | N-2-(2,4-dichloro-phenoxy)propionyl-4-bromopyrazole | 2-(2,4-dichloro-phenoxy) propionic acid (available from TCI Co.) | 4-bromopyrazole |
| (9) | N-2-(4-chloro-phenoxy) propionyl-4-bromopyrazole | 2-(4-chloro phenoxy)propionic acid (available from Sigma Co.) | 4-bromopyrazole |
| (10) | N-2-(3-phenoxyphenyl) propionyl-1,2,4-triazole | calcium 2-(3-phenoxy phenyl)propionate (available from Sigma Co.) | N,N-carbonyldi(1,2,4-triazole) |
| (11) | N-2-(4-fluoro-biphenyl) propionyl-1,2,4-triazole | 2-(4-fluoro-biphenyl) propionic acid (available from Sigma Co.) | N,N-carbonyldi(1,2,4-triazole) |
| (12) | N-2-(4-iso-butylphenyl) propionyl-1,2,4-triazole | 2-(4-isobutyl-phenyl) propionic acid (available from Sigma Co.) | N,N-carbonyldi(1,2,4-triazole) |
| (13) | N-2-(3-benzoylphenyl) propionyl-1,2,4-triazole | 2-(3-benzoyl-phenyl) propionic acid (available from TCI Co.) | N,N-carbonyldi(1,2,4-triazole) |
| (14) | N-2-(6-methoxy-naphthyl)propionyl-1,2,4-triazole | 2-(6-methoxy-naphthyl) propionic acid (available from TCI Co.) | N,N-carbonyldi(1,2,4-triazole) |
| (15) | N-α-bromo-phenylacetyl-4-bromopyrazole | α-bromophenyl-acetic acid (available from Aldrich Co.) | 4-bromopyrazole |
| (16) | N-α-methoxy-phenylacetyl-4-bromopyrazole | α-methoxyphenyl-acetic acid (available from TCI Co.) | 4-bromopyrazole |
| (17) | N-α-methoxy-phenylacetyl-3-(2-pyridinyl)pyrazole | α-methoxyphenyl-acetic acid | 3-(2-pyridinyl)pyrazole |
| (18) | N-β-phenyl-butyryl-4-bromopyrazole | β-phenylbutyric acid (available from TCI Co.) | 4-bromopyrazole |
| (19) | N-α-bromo-phenyl acetyl-1,2,4-triazole | α-bromophenyl-acetic acid | N,N-carbonyldi(1,2,4-triazole) |
| (20) | N-2-phenyl propionyl-3-aminopyrazole | 2-phenylpropionic acid | 3-aminopyrazole (available from Alfa Aesar Co.) |
| (21) | N-2-phenyl propionyl-3-methylpyrazole | 2-phenylpropionic acid | 3-methyl-pyrazole (available from Alfa Aesar Co.) |
| (22) | N-2-phenylpropionyl-3-(3-bromophenyl) pyrazole | 2-phenylpropionic acid | 3-(3-bromo-phenyl) pyrazole (available from Alfa Aesar Co.) |
| (23) | N-2-phenylpropionyl-3-methyl-4-bromo-pyrazole | 2-phenylpropionic acid | 3-methyl-4-bromo-pyrazole (available from Alfa Aesar Co.) |
| (24) | N-α-ethylphenyl acetyl-3-(2-pyridinyl) pyrazole | α-ethylphenyl-acetic acid (available from TCI Co.) | 3-(2-pyridinyl)pyrazole |
| (25) | N-α-ethylphenyl acetyl-1,2,4-triazole | α-ethylphenyl-acetic acid | N,N-carbonyldi(1,2,4-triazole) |
| (26) | N-α-methoxyphenyl acetyl-1,2,4-triazole | α-methoxyphenyl-acetic acid | N,N-carbonyldi(1,2,4-triazole) |
| (27) | N-α-bromophenyl acetyl-3-methyl-pyrazole | α-bromophenyl-acetic acid | 3-methyl-pyrazole |
| (28) | N-2-(4-fluoro-biphenyl) propionyl-4-bromopyrazole | 2-(4-fluoro-biphenyl) propionic acid | 4-bromopyrazole |

TABLE 1-continued

| No. | Racemic Substrate | Reactant (I) | (II) |
|---|---|---|---|
| (29) | N-2-(3-benzoyl-phenyl)propionyl-4-bromo-pyrazole | N-2-(3-benzoyl-phenyl) propionic acid | 4-bromopyrazole |
| (30) | N-2-(6-methoxy-naphthyl)propionyl-4-bromopyrazole | N-2-(6-methoxy-naphthyl)propionic acid | 4-bromopyrazole |

2. Lipase:
 (1) *Candida rugosa* lipase (MY) available from Japan Meito Sangyo Co., model name: Lipase MY.
 (2) *Pseudomonas cepacia* lipase (PS-C) carried on ceramic and available from Japan Amano Co., model name: Lipase PS-C Amano I.
 (3) *Pseudomonas cepacia* lipase (PS-D) carried on diatomite and available from Japan Amano Co., model name: Lipase PS-D Amano I.
 (4) *Candida antartica* lipase B (Novozym) carried on poly(acrylic acid) and available from Denmark Novo Nordisk Co., model name: NOVOZYM® 435.
 (5) *Carica papaya* lipase (pCPL) made from Taiwan Challenge Bioproducts Co., Ltd.
3. Solvent System:
 (1) Anhydrous methyl t-butyl ether was prepared by adding $CaH_2$ (available from Riedel-de Haen Co.) into methyl t-butyl ether (available from Tedia Co.) under stirring for 24 hours.
 (2) Organic solvents saturated with water were prepared by adding an appropriate amount of deionized water into the following solvents: methyl t-butyl ether, isooctane, hexane, cyclohexane, isopropyl ether and cyclohexanone (available from Tedia Co.) under stirring for 24 hours.

EXAMPLES 1-55

Hydrolytic Resolution of the Azolide Substrates (Ex1~Ex55)

The hydrolytic resolution of the substrate in each of Ex1~Ex55 was conducted and analyzed by the following steps:
1. Preparation of Reaction Solution:
 A substrate solution with a concentration of 3 mM was prepared by mixing an organic solvent saturated with water and a substrate specified in Table 2 for each Example.
 An amount of a lipase specified in Table 2 for each Example was added into 10 mL of the substrate solution so as to form a reaction solution for each Example. The reaction solution of each Example was subjected to hydrolytic resolution at a reaction temperature for a predetermined time period (see Table 2).

2. Sampling and Analyzing:
 Aliquot (200 µL) of reaction solution was taken out at predetermined time intervals and was subjected to HPLC analysis using a selected column under analyzing conditions and instrument settings shown in Table 2 and 3. The HPLC analysis results were used to calculate variables ($X_R$, $X_S$, $X_t$, E, and ee) using the following formulas:
 (1) Conversion of R- or S-stereoisomers at time t($X_R$ or $X_S$):

$$X_S = 1 - \frac{(S_S)_t}{(S_S)_0}, \quad X_R = 1 - \frac{(S_R)_t}{(S_R)_0},$$

wherein $(S_S)_0$ is the initial S-substrate concentration, $(S_S)_t$ is the S-substrate concentration at time t(hr), $(S_R)_0$ is the initial R-substrate concentration, and $(S_R)_t$ is the R-substrate concentration at time t(hr).
 (2) Conversion of the racemic mixture of the substrate ($X_t$):

$$X_t = \frac{X_S + X_R}{2}.$$

(3) Enantiomeric ratio (E):

$$E = \frac{(V_S/E_t)}{(V_R/E_t)} \text{ or } \frac{(V_R/E_t)}{(V_S/E_t)},$$

wherein $V_R$ and $V_S$ (mM/h) are the initial reaction rates for R- or S-stereoisomers, respectively, and $E_t$ is the enzyme concentration (mg/mL) of the reaction solution. The higher the E and $V_S/E_t$ or $V_R/E_t$, the higher will be the lipase enantioselectivity and reactivity, which leads to a lower cost for the preparation of the optically active compound.
 (4) Enantiomeric excess for substrate (ee):

$$ee = |[X_R - X_S]/[2 - X_R - X_S]|.$$

The calculated results are shown in Table 4.

COMPARATIVE EXAMPLE

The procedure and conditions in kinetic resolution of a substrate of Comparative Example (CE) were similar to those of Ex8, except that in CE, the solvent system was cyclohexane saturated with water and the substrate was methyl 2-phenyl-propionate. The test conditions and the calculated results are shown in Tables 2, 3 and 4, respectively.

TABLE 2

| No. | Substrate | Organic Solvent saturated with water | Enzyme/Amount (mg) | Temp. (° C.) | HPLC Analyzing Condition* | Time (h) |
|---|---|---|---|---|---|---|
| Ex1 | (1) | i-octane | Novozym/ 20 | 45 | A | 0.4 |
| Ex2 | | hexane | | 45 | | 0.5 |
| Ex3 | | cyclohexane | | 45 | | 0.7 |
| Ex4 | | i-propylether | | 45 | | 1.0 |
| Ex5 | | methyl t-butylether | | 15 | | 6.0 |
| Ex6 | | | | 25 | | 2.3 |
| Ex7 | | | | 35 | | 1.1 |

TABLE 2-continued

| No. | Substrate | Organic Solvent saturated with water | Enzyme/ Amount (mg) | Temp. (° C.) | HPLC Analyzing Condition* | Time (h) |
|---|---|---|---|---|---|---|
| Ex8 | | | | 45 | | 0.7 |
| Ex9 | | | | 55 | | 0.5 |
| Ex10 | | cyclohexanone | | 45 | | 5.0 |
| EX11 | (1) | cyclohexane | MY/100 | 45 | A | 2.0 |
| CE | Methyl 2-phenyl propionate | methyl t-butylether | Novozym/20 | 45 | A | 9.0 |
| Ex12 | (2) | cyclohexane | MY/200 | 45 | L | 5.0 |
| Ex13 | | | PS-C/100 | 45 | | 4.0 |
| Ex14 | | | PS-D/200 | 45 | | 25.0 |
| Ex15 | | | Novozym/120 | 45 | | 1.0 |
| Ex16 | | | pCPL/100 | 45 | | 25.0 |
| Ex17 | (3) | cyclohexane | MY/200 | 45 | C | 5.0 |
| Ex18 | (4) | cyclohexane | MY/200 | 45 | C | 1.0 |
| Ex19 | (5) | methyl t-butylether | Novozym/200 | 45 | H | 4.3 |
| Ex20 | (6) | methyl t-butylether | Novozym/20 | 45 | C | 1.0 |
| Ex21 | (3) | methyl t-butylether | Novozym/200 | 45 | C | 0.8 |
| Ex22 | (4) | methyl t-butylether | Novozym/200 | 45 | C | 0.3 |
| Ex23 | (7) | methyl t-butylether | Novozym/100 | 45 | M | 24.0 |
| Ex24 | (8) | methyl t-butylether | Novozym/100 | 45 | P | 0.4 |
| Ex25 | (9) | methyl t-butylether | Novozym/20 | 45 | Q | 1.5 |
| Ex26 | (10) | methyl t-butylether | Novozym/20 | 45 | I | 4.5 |
| Ex27 | (11) | methyl t-butylether | Novozym/100 | 45 | K | 5.0 |
| Ex28 | (12) | methyl t-butylether | Novozym/20 | 45 | P | 21.0 |
| Ex29 | (13) | methyl t-butylether | Novozym/20 | 45 | J | 1.7 |
| Ex30 | (14) | methyl t-butylether | Novozym/60 | 45 | J | 3.0 |
| Ex31 | (15) | cyclohexane | Novozym/120 | 45 | A | 4.0 |
| Ex32 | (15) | methyl t-butylether | Novozym/200 | 45 | A | 12.0 |
| EX33 | (15) | cyclohexane | MY/200 | 45 | A | 4.0 |
| Ex34 | (16) | cyclohexane | Novozym/60 | 45 | N | 3.0 |
| EX35 | (16) | cyclohexane | MY/100 | 45 | N | 0.6 |
| Ex36 | (17) | methyl t-butylether | Novozym/200 | 45 | F | 48.0 |
| EX37 | (17) | cyclohexane | MY/600 | 45 | F | 9.0 |
| Ex38 | (18) | cyclohexane | Novozym/200 | 45 | N | 8.0 |
| EX39 | (20) | methyl t-butylether | Novozym/200 | 45 | O | 5.0 |
| EX40 | (20) | cyclohexane | MY/400 | 45 | O | 5.0 |
| EX41 | (21) | methyl t-butylether | Novozym/200 | 45 | B | 4.0 |
| EX42 | (21) | cyclohexane | MY/400 | 45 | B | 72.0 |
| EX43 | (22) | methyl t-butylether | Novozym/400 | 45 | B | 48.0 |
| EX44 | (23) | methyl t-butylether | Novozym/600 | 45 | D | 18.0 |
| EX45 | (24) | methyl t-butylether | Novozym/400 | 45 | D | 147.5 |
| EX46 | (25) | methyl t-butylether | Novozym/100 | 45 | B | 2.0 |
| EX47 | (26) | methyl t-butylether | Novozym/20 | 45 | O | 1.3 |
| EX48 | (27) | methyl t-butylether | Novozym/200 | 45 | G | 9.5 |
| EX49 | (27) | cyclohexane | MY/400 | 45 | G | 2.0 |
| EX50 | (28) | methyl t-butylether | Novozym/400 | 45 | E | 24.0 |

TABLE 2-continued

| No. | Substrate | Organic Solvent saturated with water | Enzyme/Amount (mg) | Temp. (°C.) | HPLC Analyzing Condition* | Time (h) |
|---|---|---|---|---|---|---|
| EX51 | (28) | cyclohexane | MY/200 | 45 | E | 20.0 |
| EX52 | (29) | methyl t-butylether | Novozym/200 | 45 | R | 2.0 |
| EX53 | (30) | methyl t-butylether | Novozym/400 | 45 | S | 19.5 |
| EX54 | (30) | cyclohexane | MY/100 | 45 | S | 22.5 |
| EX55 | (19) | methyl t-butylether | Novozym/20 | 45 | L | 3.0 |

*HPLC analyzing conditions are shown in Table 3

TABLE 3

HPLC Analyzing Condition

| No. | Mobile phase | Flow rate (mL/min) | Wavelength (nm) | Column |
|---|---|---|---|---|
| A | I:II = 90:10 | 2.0 | 220 | OJ-H column available from Daicel Co. |
| B | I:II = 90:10 | 2.0 | 270 | |
| C | I:II = 95:5 | 2.0 | 220 | |
| D | I:II = 98:2 | 2.0 | 270 | |
| E | I:II = 95:5 | 2.0 | 270 | |
| F | I:II = 70:30 | 2.0 | 270 | |
| G | I:II = 60:40 | 2.0 | 270 | |
| H | I:II:III = 69.5:30:0.5 | 2.0 | 220 | |
| I | I:II:III = 89.5:10:0.5 | 1.5 | 270 | |
| J | I:II:III = 89.5:10:0.5 | 2.0 | 270 | |
| K | I:II:III = 94.5:5:0.5 | 2.0 | 270 | |
| L | I:II = 95:5 | 2.0 | 220 | OD-H column available from Daicel Co. |
| M | I:II = 95:5 | 1.5 | 270 | |
| N | I:II = 90:10 | 2.0 | 270 | |
| O | I:II = 90:10 | 2.0 | 220 | |
| P | I:II = 97:3 | 2.0 | 270 | |
| Q | I:II = 97:3 | 2.0 | 270 | (S,S) WHELK-01 column available from Regis Co. |
| R | I:II = 95:5 | 2.0 | 270 | |
| S | I:II = 90:10 | 2.0 | 270 | |

I: n-hexane;
II: i-propanol;
III: acetic acid

TABLE 4

| No. | $V_R/E_t$ (mmol/hg) | $V_S/E_t$ (mmol/hg) | $E_t$(mg/mL) | $X_t$ (%) | E | ee (%) |
|---|---|---|---|---|---|---|
| Ex1 | 9.17 | $4.76 \times 10^{-1}$ | 2.0 | 58.8 | 19.3 | 100.0 |
| Ex2 | 7.52 | $2.16 \times 10^{-1}$ | 2.0 | 59.5 | 34.8 | 100.0 |
| Ex3 | 5.20 | $1.23 \times 10^{-1}$ | 2.0 | 54.6 | 42.3 | 100.0 |
| Ex4 | 4.31 | $6.78 \times 10^{-2}$ | 2.0 | 52.0 | 63.5 | 100.0 |
| Ex5 | 1.32 | $6.75 \times 10^{-3}$ | 2.0 | 55.3 | 196.8 | 100.0 |
| Ex6 | 1.91 | $1.51 \times 10^{-2}$ | 2.0 | 50.9 | 126.9 | 100.0 |
| Ex7 | 3.54 | $3.50 \times 10^{-2}$ | 2.0 | 51.6 | 101.3 | 100.0 |
| Ex8 | 4.38 | $4.58 \times 10^{-2}$ | 2.0 | 55.6 | 95.6 | 100.0 |
| Ex9 | 7.78 | $1.17 \times 10^{-1}$ | 2.0 | 53.6 | 66.7 | 100.0 |
| Ex10 | $5.67 \times 10^{-1}$ | $1.27 \times 10^{-2}$ | 6.0 | 66.6 | 44.6 | 100.0 |
| EX11 | $2.92 \times 10^{-2}$ | $3.94 \times 10^{-1}$ | 10.0 | 54.6 | 13.5 | 82.9 |
| CE | $1.10 \times 10^{-1}$ | $2.34 \times 10^{-2}$ | 2.0 | 44.5 | 4.7 | 48.1 |
| Ex12 | $8.10 \times 10^{-4}$ | $9.86 \times 10^{-3}$ | 20.0 | 54.8 | 121.7 | 100.0 |
| Ex13 | $7.38 \times 10^{-2}$ | $1.00 \times 10^{-2}$ | 10.0 | 51.6 | 7.4 | 68.5 |
| Ex14 | $2.58 \times 10^{-2}$ | $2.70 \times 10^{-4}$ | 20.0 | 54.0 | 95.6 | 100.0 |
| Ex15 | $6.99 \times 10^{-1}$ | $1.01 \times 10^{-2}$ | 12.0 | 51.3 | 69.0 | 100.0 |
| Ex16 | $1.14 \times 10^{-3}$ | $1.97 \times 10^{-2}$ | 10.0 | 55.6 | 17.2 | 79.8 |
| Ex17 | $6.78 \times 10^{-4}$ | $8.47 \times 10^{-2}$ | 20.0 | 52.8 | 124.9 | 100.0 |
| Ex18 | $8.95 \times 10^{-3}$ | $4.61 \times 10^{-1}$ | 20.0 | 53.1 | 51.6 | 100.0 |
| Ex19 | $2.88 \times 10^{-2}$ | $4.76 \times 10^{-3}$ | 20.0 | 51.8 | 6.1 | 58.8 |
| Ex20 | 2.62 | $3.23 \times 10^{-2}$ | 2.0 | 53.5 | 81.3 | 100.0 |
| Ex21 | $5.28 \times 10^{-1}$ | $4.73 \times 10^{-3}$ | 20.0 | 51.0 | 111.7 | 100.0 |
| Ex22 | 1.61 | $6.62 \times 10^{-3}$ | 20.0 | 50.1 | 243.4 | 100.0 |
| Ex23 | $1.79 \times 10^{-2}$ | $5.70 \times 10^{-5}$ | 10.0 | 45.2 | 314.2 | 82.1 |
| Ex24 | $1.72 \times 10^{-2}$ | 1.64 | 10.0 | 50.8 | 95.6 | 100.0 |
| Ex25 | $7.24 \times 10^{-2}$ | 2.26 | 2.0 | 54.5 | 31.2 | 100.0 |
| Ex26 | 2.55 | $1.80 \times 10^{-2}$ | 2.0 | 52.3 | 141.6 | 100.0 |
| Ex27 | $1.54 \times 10^{-1}$ | $2.16 \times 10^{-3}$ | 10.0 | 55.8 | 71.1 | 100.0 |
| Ex28 | $3.03 \times 10^{-1}$ | $1.61 \times 10^{-3}$ | 2.0 | 51.8 | 188.2 | 100.0 |
| Ex29 | 2.99 | $3.22 \times 10^{-2}$ | 2.0 | 53.1 | 92.8 | 100.0 |
| Ex30 | $2.60 \times 10^{-1}$ | $3.18 \times 10^{-3}$ | 6.0 | 53.3 | 81.8 | 100.0 |
| Ex31 | $4.52 \times 10^{-2}$ | $1.59 \times 10^{-3}$ | 12.0 | 37.7 | 28.5 | 53.2 |
| EX32 | $6.04 \times 10^{-3}$ | $2.63 \times 10^{-3}$ | 20.0 | 50.3 | 23.0 | 78.9 |
| EX33 | $1.69 \times 10^{-3}$ | $8.90 \times 10^{-2}$ | 20.0 | 53.4 | 52.6 | 100.0 |
| Ex34 | $5.23 \times 10^{-1}$ | $8.75 \times 10^{-3}$ | 6.0 | 55.5 | 59.8 | 100.0 |
| EX35 | $7.33 \times 10^{-2}$ | 1.08 | 10.0 | 58.1 | 14.7 | 96.2 |
| Ex36 | $5.92 \times 10^{-3}$ | $1.73 \times 10^{-5}$ | 20.0 | 51.8 | 342.2 | 100.0 |
| Ex37 | $2.40 \times 10^{-1}$ | $8.92 \times 10^{-3}$ | 60.0 | 51.5 | 37.2 | 89.2 |
| Ex38 | $5.37 \times 10^{-2}$ | $1.09 \times 10^{-3}$ | 20.0 | 55.2 | 49.4 | 100.0 |
| EX39 | $6.57 \times 10^{-2}$ | $3.35 \times 10^{-4}$ | 20.0 | 51.4 | 196.1 | 100.0 |
| EX40 | $5.14 \times 10^{-4}$ | $3.44 \times 10^{-2}$ | 40.0 | 53.2 | 66.9 | 100.0 |
| EX41 | $9.05 \times 10^{-2}$ | $5.62 \times 10^{-4}$ | 20.0 | 51.5 | 161.0 | 100.0 |
| EX42 | $1.16 \times 10^{-5}$ | $4.79 \times 10^{-3}$ | 40.0 | 42.8 | 41.3 | 68.0 |
| EX43 | $3.62 \times 10^{-3}$ | $1.76 \times 10^{-5}$ | 40.0 | 51.1 | 291.5 | 100.0 |
| EX44 | $1.32 \times 10^{-2}$ | $5.00 \times 10^{-5}$ | 60.0 | 51.8 | 264.0 | 100.0 |
| EX45 | $8.85 \times 10^{-4}$ | — | 40.0 | 48.5 | — | 94.2 |
| EX46 | $4.25 \times 10^{-1}$ | $2.25 \times 10^{-3}$ | 10.0 | 51.5 | 188.9 | 100.0 |
| EX47 | 1.88 | $2.54 \times 10^{-1}$ | 2.0 | 68.3 | 7.4 | 100.0 |
| EX48 | $2.41 \times 10^{-2}$ | $9.75 \times 10^{-5}$ | 20.0 | 50.8 | 247.2 | 100.0 |
| EX49 | $1.89 \times 10^{-3}$ | $1.11 \times 10^{-1}$ | 40.0 | 53.0 | 58.7 | 100.0 |
| EX50 | $1.79 \times 10^{-3}$ | $8.63 \times 10^{-5}$ | 40.0 | 54.7 | 207.4 | 100.0 |
| EX51 | $1.16 \times 10^{-3}$ | $7.24 \times 10^{-2}$ | 20.0 | 59.5 | 62.3 | 100.0 |
| EX52 | $2.15 \times 10^{-1}$ | $8.25 \times 10^{-4}$ | 20.0 | 50.5 | 260.6 | 100.0 |
| EX53 | $2.31 \times 10^{-2}$ | $2.10 \times 10^{-4}$ | 40.0 | 57.5 | 110.0 | 100.0 |
| EX54 | $2.37 \times 10^{-2}$ | $7.56 \times 10^{-2}$ | 10.0 | 62.6 | 31.9 | 87.5 |
| EX55 | 1.15 | $9.05 \times 10^{-2}$ | 2.0 | 64.4 | 12.8 | 100.0 |

— not detected

In Table 4, the conversion $X_t$ of Ex1~Ex55 is from 37.7% to 68.3%, E is from 4.7 to 342.2, and ee is from 48.1% to 100.0%.

Comparing Ex8 with CE, the E value of Ex8 is 20 times that of CE; and the ee value of Ex8 is 100%, while that of CE is 48.1%, which shows that the conversion of Ex8 is higher and the reaction time of Ex8 is shorter as compared to those of CE.

EXAMPLES 56-95

Alcoholytic Resolution of Azolide Substrates (Ex56~Ex95)

The alcoholytic resolution of the substrate for each of Ex56~Ex95 was conducted and analyzed by the following steps:
1. Preparation of Reaction Solution:
For each Example (with reference to Table 5), anhydrous methyl t-butylether was mixed with a substrate so as to obtain a substrate solution with a concentration of 3 mM, and with an alcohol so as to obtain 100 mM of an alcohol solution.

Novozym and the alcohol solution were added into 10 mL of the substrate solution so as to form a reaction solution for each Example. The reaction solution was subjected to alcoholytic resolution at a temperature for a predetermined time period (see Table 5).

2. Sampling and Analyzing:

Sampling and analyzing (the analysis conditions and settings are shown in Table 5) of Ex56-Ex95 were conducted in the same manner as those of Ex1~Ex55. The calculated results of the $X_t$ value, the E value and the ee value according to the above formulas for each Example are shown in Table 6.

TABLE 5

| Ex | Substrate | Alcohol | Amount of enzyme (mg) | Temp. (° C.) | HPLC analyzing parameters | Time (h) |
|---|---|---|---|---|---|---|
| 56 | (1) | methanol | 20 | 45 | A | 0.6 |
| 57 |  | n-hexanol | 20 | 45 |  | 1.0 |
| 58 |  | trimethylsilyl methanol | 20 | 45 |  | 0.2 |
| 59 |  | trimethylsilyl ethanol | 20 | 45 |  | 0.2 |
| 60 |  | dimethylamino ethanol | 5 | 45 |  | 0.5 |
| 61 | (2) | methanol | 100 | 45 | L | 0.3 |
| 62 | (7) | methanol | 20 | 45 | M | 5.0 |
| 63 | (10) | methanol | 20 | 45 | I | 2.0 |
| 64 | (11) | methanol | 120 | 25 | K | 1.0 |
| 65 |  | methanol | 120 | 35 |  | 3.0 |
| 66 |  | methanol | 60 | 45 |  | 3.0 |
| 67 |  | methanol | 60 | 55 |  | 2.0 |
| 68 |  | ethanol | 20 | 45 |  | 5.0 |
| 69 |  | n-propanol | 60 | 45 |  | 1.0 |
| 70 |  | n-butanol | 20 | 45 |  | 3.7 |
| 71 |  | n-pentanol | 20 | 45 |  | 9.0 |
| 72 |  | n-hexane | 60 | 45 |  | 1.0 |
| 73 | (12) | methanol | 20 | 45 | P | 8.0 |
| 74 | (13) | methanol | 20 | 45 | J | 1.0 |
| 75 | (14) | methanol | 60 | 35 | J | 3.0 |
| 76 |  | methanol |  | 45 |  | 2.2 |
| 77 |  | methanol |  | 55 |  | 2.0 |
| 78 |  | ethanol |  | 45 |  | 2.2 |
| 79 |  | n-propanol |  | 45 |  | 4.1 |
| 80 |  | n-butanol |  | 45 |  | 4.1 |
| 81 |  | n-pentanol |  | 45 |  | 2.2 |
| 82 |  | n-hexanol |  | 45 |  | 2.2 |
| 83 | (19) | methanol | 20 | 45 | L | 1.0 |
| 84 | (16) | methanol | 20 | 45 | N | 1.3 |
| 85 | (17) | methanol | 20 | 45 | F | 3.1 |
| 86 | (18) | methanol | 200 | 45 | N | 1.0 |
| 87 | (20) | methanol | 20 | 45 | O | 3.0 |
| 88 | (21) | methanol | 100 | 45 | B | 1.0 |
| 89 | (22) | methanol | 20 | 45 | B | 20.0 |
| 90 | (23) | methanol | 100 | 45 | D | 6.0 |
| 91 | (24) | methanol | 100 | 45 | D | 2.0 |
| 92 | (25) | methanol | 20 | 45 | B | 3.5 |
| 93 | (26) | methanol | 20 | 45 | O | 0.3 |
| 94 | (27) | methanol | 100 | 45 | G | 3.5 |
| 95 | (28) | methanol | 60 | 45 | E | 1.5 |

TABLE 6

| Ex | $V_R/E_t$ (mmol/hg) | $V_S/E_t$ (mmol/hg) | $E_t$ (mg/mL) | $X_t$ (%) | E | ee (%) |
|---|---|---|---|---|---|---|
| 56 | 9.46 | $2.15 \times 10^{-1}$ | 2.0 | 60.0 | 43.9 | 100.0 |
| 57 | 6.16 | $1.43 \times 10^{-1}$ | 2.0 | 60.0 | 43.1 | 100.0 |
| 58 | 12.8 | $7.30 \times 10^{-1}$ | 2.0 | 56.6 | 17.5 | 90.1 |
| 59 | 11.6 | $8.82 \times 10^{-1}$ | 2.0 | 54.7 | 13.2 | 84.3 |
| 60 | 11.63 | $9.03 \times 10^{-1}$ | 0.5 | 59.1 | 18.1 | 100.0 |
| 61 | 2.98 | $3.79 \times 10^{-2}$ | 10.0 | 50.4 | 78.6 | 100.0 |
| 62 | 1.99 | $2.40 \times 10^{-3}$ | 2.0 | 50.9 | 828.1 | 100.0 |
| 63 | 4.94 | $4.94 \times 10^{-2}$ | 2.0 | 55.0 | 100.0 | 100.0 |
| 64 | $3.11 \times 10^{-1}$ | $3.04 \times 10^{-3}$ | 12.0 | 51.3 | 102.3 | 100.0 |
| 65 | $7.66 \times 10^{-1}$ | $8.28 \times 10^{-3}$ | 12.0 | 58.0 | 92.6 | 100.0 |
| 66 | 1.08 | $1.31 \times 10^{-2}$ | 6.0 | 56.1 | 82.5 | 100.0 |
| 67 | 1.79 | $2.38 \times 10^{-2}$ | 6.0 | 58.1 | 75.3 | 100.0 |
| 68 | $6.20 \times 10^{-1}$ | $6.72 \times 10^{-3}$ | 2.0 | 51.6 | 92.3 | 100.0 |
| 69 | $7.60 \times 10^{-1}$ | $8.10 \times 10^{-3}$ | 6.0 | 51.7 | 93.8 | 100.0 |
| 70 | $6.28 \times 10^{-1}$ | $6.68 \times 10^{-3}$ | 2.0 | 50.2 | 94.0 | 100.0 |
| 71 | $9.17 \times 10^{-1}$ | $9.83 \times 10^{-3}$ | 2.0 | 57.4 | 93.3 | 100.0 |
| 72 | $7.53 \times 10^{-1}$ | $7.38 \times 10^{-3}$ | 6.0 | 51.0 | 102.0 | 100.0 |
| 73 | 1.29 | $1.13 \times 10^{-2}$ | 2.0 | 52.1 | 114.1 | 100.0 |
| 74 | 3.96 | $6.25 \times 10^{-2}$ | 2.0 | 51.4 | 63.4 | 100.0 |
| 75 | $4.82 \times 10^{-1}$ | $4.00 \times 10^{-3}$ | 6.0 | 52.4 | 120.4 | 100.0 |
| 76 | $9.79 \times 10^{-1}$ | $9.25 \times 10^{-3}$ | 6.0 | 52.4 | 105.7 | 100.0 |
| 77 | 1.30 | $1.63 \times 10^{-2}$ | 6.0 | 55.2 | 80.0 | 100.0 |
| 78 | 1.01 | $1.07 \times 10^{-2}$ | 6.0 | 54.0 | 94.4 | 100.0 |
| 79 | $9.23 \times 10^{-1}$ | $8.79 \times 10^{-3}$ | 6.0 | 52.9 | 105.0 | 100.0 |
| 80 | $8.62 \times 10^{-1}$ | $9.75 \times 10^{-3}$ | 6.0 | 54.8 | 88.4 | 100.0 |
| 81 | 1.18 | $1.15 \times 10^{-2}$ | 6.0 | 53.5 | 102.7 | 100.0 |
| 82 | 1.17 | $1.10 \times 10^{-2}$ | 6.0 | 53.0 | 106.6 | 100.0 |
| 83 | 3.60 | $1.13 \times 10^{-1}$ | 2.0 | 54.6 | 32.0 | 100.0 |
| 84 | 2.36 | $6.62 \times 10^{-2}$ | 2.0 | 54.4 | 35.8 | 100.0 |
| 85 | $6.82 \times 10^{-1}$ | $2.76 \times 10^{-3}$ | 2.0 | 51.4 | 247.0 | 100.0 |
| 86 | $2.74 \times 10^{-1}$ | $1.27 \times 10^{-2}$ | 20.0 | 53.7 | 21.5 | 100.0 |
| 87 | 1.06 | $3.05 \times 10^{-3}$ | 2.0 | 50.7 | 347.5 | 100.0 |
| 88 | $9.69 \times 10^{-1}$ | $3.63 \times 10^{-3}$ | 10.0 | 50.6 | 266.9 | 100.0 |
| 89 | $7.99 \times 10^{-1}$ | $1.08 \times 10^{-3}$ | 2.0 | 51.1 | 739.8 | 100.0 |
| 90 | $5.07 \times 10^{-1}$ | $1.82 \times 10^{-3}$ | 10.0 | 50.4 | 278.6 | 100.0 |
| 91 | $1.56 \times 10^{-1}$ | $1.40 \times 10^{-4}$ | 20.0 | 50.2 | 1114.3 | 100.0 |
| 92 | 1.63 | $1.43 \times 10^{-2}$ | 2.0 | 50.1 | 114.0 | 100.0 |
| 93 | 5.60 | 1.09 | 2.0 | 64.8 | 5.1 | 72.1 |
| 94 | $3.07 \times 10^{-1}$ | $2.03 \times 10^{-3}$ | 10.0 | 50.6 | 133.5 | 100.0 |
| 95 | $6.01 \times 10^{-1}$ | $4.58 \times 10^{-3}$ | 6.0 | 52.1 | 131.2 | 100.0 |

In Table 6, the conversion $X_t$ of Ex56~Ex95 is from 50.1% to 64.8%, the E value is from 5.1 to 1114.3, and the ee value is from 72.1% to 100.0%.

In conclusion, the method for producing an optically active compound of this invention utilizes the azolide substrate, which contains an azole group used as a leaving group, to subject to an enzyme-catalyzed kinetic resolution, so as to enhance conversion, E and ee values, and also decrease the reaction time.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. A method for producing an optically active compound, comprising: reacting a nucleophile with a mixture of R- and S-stereoisomers of an azolide substrate by enzyme-catalyzed kinetic resolution so as to produce the optically active compound, wherein the azolide substrate contains an azole group used as a leaving group and an acyl group directly bonded to a nitrogen atom of the azole group, wherein the azolide substrate is represented by Formula (I):

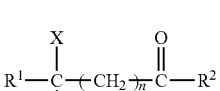

wherein

X represents a halogen atom, methyl, ethyl, methoxy, etjpxu. —OH, —NH$_2$, —NHCOCH$_3$, —SH, or —SCH$_3$;

R$^1$ is different from X and represents a straight-chain or branched saturated or unsaturated C$_1$-C$_{20}$ aliphatic group, an aryl an aryloxy group or a C$_3$-C$_{12}$ heterocyclic group containing one to three heteroatoms selected from the group consisting of O, S and N, each group being optionally substituted with one to three substituents selected from the group consisting of a halogen atom, an aryl group, an aryloxy group, $-NH_2$, $-CF_3$, $-CN$, $-NO_2$, $-OH$, $-SH$, $-COOH$, $-SCF_3$, $-OCF_3$, $-CONH_2$, $-COC_6H_5$, a $C_1$-$C_6$ alkyl group and a $C_1$-$C_6$ alkoxy group;

$R^2$ represents an azole group optionally substituted with one substituent or two substituents selected from the group consisting of a halogen atom, an aryl group, an aryloxy group, $-NH_2$, $-CF_3$, $-CN$, $-NO_2$, $-OH$, $-SH$, $-COOH$, $-SCF_3$, $-OCF_3$, $-CONH_2$, a $C_1$-$C_6$alkyl group and a $C_1$-$C_6$ alkoxy group; and n is 0 or 1.

2. The method of claim 1, wherein the enzyme-catalyzed kinetic resolution is conducted in an organic solvent in the presence of a lipase.

3. The method of claim 1, wherein the azolide substrate is a racemic mixture of the R- and S-stereoisomers.

4. The method of claim 1, wherein X of Formula (I) represents a halogen atom, methyl, ethyl, methoxy, or ethoxy.

5. The method of claim 4, wherein X represents Br, methyl, ethyl, or methoxy.

6. The method of claim 1, wherein $R^1$ of Formula (I) represents an optionally substituted aryl group, or a substituted aryloxy group.

7. The method of claim 6, wherein $R^1$ represents an optionally substituted phenyl group, an optionally substituted phenoxy group, or an optionally substituted naphthyl group.

8. The method of claim 7, wherein $R^1$ represents phenyl, 2,4-dichlorophenoxy, 4-chlorophenoxy, 3-phenoxyphenyl, 4-fluorobiphenyl, 4-isobutylphenyl, 3-benzoylphenyl, or 6-methoxynaphthyl.

9. The method of claim 1, wherein $R^2$ of Formula (I) represents an optionally substituted imidazolyl group, an optionally substituted pyrazolyl group, an optionally substituted triazolyl group, or an optionally substituted tetrazolyl group.

10. The method of claim 1, wherein $R^2$ represents 1,2,4-triazolyl, 4-bromopyrazolyl, 4-methylpyrazolyl, 4-nitropyrazolyl, imidazolyl, pyrazolyl, 3-(2-pyridyl)pyrazolyl, 3-aminopyrazolyl, 3-methylpyrazolyl, 3-(3-bromophenyl)pyrazolyl, or 3-methyl-4-bromopyrazolyl.

11. The method of claim, wherein the azolide substrate is selected from the group consisting of:
N-2-phenylpropionyl-1,2,4-triazole,
N-2-phenylpropionyl-4-bromopyrazole,
N-2-phenylpropionyl-4-methylpyrazole,
N-2-phenylpropionyl-4-nitropyrazole,
N-2-phenylpropionyl-imidazole,
N-2-phenylpropionyl-pyrazole,
N-2-phenylpropionyl-3-(2-pyridinyl)pyrazole,
N-2-(2,4-dichlorophenoxy)propionyl-4-bromopyrazole,
N-2-(4-chlorophenoxy)propionyl-4-bromopyrazole,
N-2-(3-phenoxyphenyl)propionyl-1,2,4-triazole,
N-2-(4-fluorobiphenyl)propionyl-1,2,4-triazole,
N-2-(4-isobutylphenyl)propionyl-1,2,4-triazole,
N-2-(3-benzoylphenyl)propionyl-1,2,4-triazole,
N-2-(6-methoxynaphthyl)propionyl-1,2,4-triazole,
N-α-bromophenylacetyl-4-bromopyrazole,
N-α-methoxyphenylacetyl-4-bromopyrazole,
N-α-methoxyphenylacetyl-3-(2-pyridinyl)pyrazole,
N-β-phenylbutyryl-4-bromopyrazole,
N-α-bromophenylacetyl-1,2,4-triazole,
N-2-phenylpropionyl-3-aminopyrazole,
N-2-phenylpropionyl-3-methylpyrazole,
N-2-phenylpropionyl-3-(3-bromophenyl)pyrazole,
N-2-phenylpropionyl-3-methyl-4-bromopyrazole,
N-α-ethyl phenylacetyl-3-(2-pyridinyl)pyrazole,
N-α-ethylphenylacetyl-1,2,4-triazole,
N-α-methoxyphenylacetyl-1,2,4-triazole,
N-α-bromophenylacetyl-3-methylpyrazole,
N-2-(4-fluorobiphenyl)propionyl-4-bromopyrazole,
N-2-(3-benzoylphenyl)propionyl-4-bromopyrazole, and
N-2-(6-methoxynaphthyl)propionyl-4-bromopyrazole.

12. The method of claim 1, wherein the nucleophile is water and the enzyme-catalyzed kinetic resolution is performed through stereoselective hydrolysis of the substrate.

13. The method of claim 1, wherein the nucleophile is an alcohol and the enzyme-catalyzed kinetic resolution is performed through stereoselective alcoholysis of the substrate.

14. The method of claim 13, wherein the alcohol is selected from the group consisting of methanol, ethanol, propanol, butanol, pentanol, hexanol, trimethylsilyl methanol, trimethylsilyl ethanol and dimethylamino ethanol.

15. The method of claim 1, wherein the enzyme-catalyzed kinetic resolution is conducted at a temperature ranging from 5° C. to 90° C.

16. The method of claim 2, wherein the lipase is selected from the group consisting of *Candida rugosa* lipase, *Pseudomonas cepacia* lipase, *Candida antarctica* lipase B, and *Carica papaya* lipase.

17. The method of claim 16, wherein the lipase is carried on a support selected from the group consisting of an organic support and an inorganic support.

18. The method of claim 2, wherein the organic solvent is selected from the group consisting of isooctane, heptane, hexane, cyclohexane, cyclohexanone, pentane, toluene, benzene, isopropyl ether, methyl isobutyl ether, methyl t-butyl ether, dichloromethane, t-pentanol, and combinations thereof.

* * * * *